United States Patent [19]

Roteman

[11] 4,033,997

[45] July 5, 1977

[54] PREPARATION OF DOPAMINE DERIVATIVES

[75] Inventor: Robert Roteman, Waukegan, Ill.

[73] Assignee: Abbott Laboratories, North Chicago, Ill.

[22] Filed: Feb. 26, 1976

[21] Appl. No.: 661,470

[52] U.S. Cl. .............. 260/463; 260/326.13 R; 260/326.85; 260/558 A; 260/558 P; 260/562 N; 260/562 S

[51] Int. Cl.$^2$ ............. C07C 68/02; C07C 69/96

[58] Field of Search ........ 260/562 N, 463, 326.85, 260/562 S, 558 A, 558 P, 471 A, 326.13 R

[56] References Cited

UNITED STATES PATENTS

| | | |
|---|---|---|
| 2,617,796 | 11/1952 | Vaughan, Jr. ............. 260/562 N X |
| 2,710,857 | 6/1955 | Vaughan, Jr. ............. 260/562 N X |
| 2,713,574 | 7/1955 | Vaughan, Jr. ............. 260/562 N X |
| 2,715,119 | 8/1955 | Wieland et al. ............ 260/562 N X |
| 2,835,704 | 5/1958 | Walton ...................... 260/562 N |
| 3,542,850 | 11/1970 | Jansen et al. ............. 260/562 N X |
| 3,676,492 | 7/1972 | Biel et al. .................. 260/559 A |
| 3,801,562 | 4/1974 | de Benneville ........... 260/562 N X |
| 3,903,077 | 9/1975 | Jones et al. ............... 260/562 N X |
| 3,907,864 | 9/1975 | Biel et al. .................. 260/562 N X |

*Primary Examiner*—Daniel E. Wyman
*Assistant Examiner*—Thomas A. Waltz
*Attorney, Agent, or Firm*—Paul D. Burgauer; Robert L. Niblack

[57] ABSTRACT

Excellent results have been obtained by reacting N-carboxyanhydrides of aminoacids with dopamine. This new route for making aminoacid derivatives of dopamine is advantageous as the aminoacid needs no blocking of the amino group and therefore no additional reaction step for the removal of such a blocking group.

10 Claims, No Drawings

PREPARATION OF DOPAMINE DERIVATIVES

DETAILED DESCRIPTION OF THE INVENTION

N-aminoacid derivatives of dopamine have found a variety of uses in the field of medicine including the preparation of useful drugs, i.e. the uses described in U.S. Pat. No. 3,676,492. However, the preparation of these compounds have always required a number of steps, primarily a reaction to attach a blocking group to the amine terminus of the aminoacid prior to the condensation step with dopamine and, of course, the blocking group had to be removed subsequent to said condensation.

In the search of a better and less cumbersome method, it has now been discovered that the compounds of the formula below can be prepared in good yields and in a single condensation reaction.

It has now been found that compounds of the formula

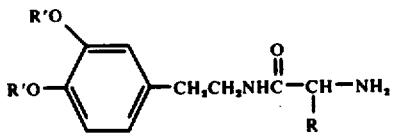

wherein R is hydrogen or an inert radical and R' is hydrogen or benzyloxycarbonyl, can be prepared by reacting substantially equimolar amounts of dopamine or 3,4-dibenzyloxycarbonyloxy phenethylamine and the N-carboxyanhydride of a natural aminoacid in the presence of a liquid, inert reaction medium at a pH of between 8 and 12.5 at a temperature of between $-10°$ C and $5°$ C. The term "inert reaction medium" is used above only to denote that said liquid does not react with any of the components in the reaction mixture. The term "inert radical" is meant to include all those commonly encountered aminoacid moieties that do not contain a functional group, i.e. alkyl groups, phenylalkyl, indolyl, alkylmercaptoalkyl or pyrrolidyl; it also includes radicals containing protected functional groups, e.g. benzyloxycarbonyl protected hydroxy groups that may be attached to an alkyl or a phenyl group included in the definition of R above.

The simplest liquid reaction medium that can be used for the above procedure is water buffered with sodium borate to the necessary pH, preferably to a pH of 10.3 $\pm 0.2$ or similarly, other liquids that can be adjusted to this pH requirement and being non-active towards the two reactants and the condensation product can be used, particularly, tetrahydrofuran, aqueous tetrahydrofuran, dioxane, or aqueous acetonitrile. Except for the case where sodium borate is used in the aqueous system for adjusting the pH, the desired pH can easily be attained by the use of sodium carbonate, sodium hydroxide or sodium bicarbonate with up to 1 molar proportion thereof. Where desired, sodium borate may be used for this purpose.

When the above condensation is carried out in the presence of water and no organic solvent is used, the N-carboxyanhydride of the aminoacid is preferably added together with the pH adjuster. This is desired because the reaction is very exothermic and almost instantaneous; however, in this instance, the aminoacid derivative is preferably added in as short a time period as practical. When an organic solvent system is used, the reaction is not as rapid and pH adjustment is not necessary during the reaction. Thus, all reactants, the condensation medium and the pH adjusters can be added in any chosen sequence to an organic solvent which still completes the reaction within about two hours. In all instances, a time period of 1-4 hours is sufficient to get complete reaction and condensation, yielding between 90 and 100% of the theoretical amount of the desired dopamine derivative of formula I.

The optimum pH range for the above reaction is between 10-11 and the optimum ratios of reactants, of course, are equimolar proportions. However, if desired and if the cost of one reactant is far greater than that of the other, the reaction itself easily allows the use of as much as a 20% or greater excess of either one of them. After an initial 30 minutes, the reaction mixture can be allowed to warm up to room temperature for faster completion of the reaction.

The current invention, aside from providing a very practical method for making the compounds of formula I, also has the significant advantage of retaining the optical configuration of the aminoacid involved where R is other than hydrogen. As many of the desired compounds of formula I favor the one or the other optical form, the present method is particularly advantageous where a compound of formula I is sought that has a distinct optical form. As the optical L-form is usually the one that shows better activity, the current process has special advantages when applied to L-aminoacids.

In order to illustrate the process of the present invention, reference is made to the following examples which, however, are not meant to limit the invention in any respect.

EXAMPLE I

To a solution of 26.2 g. of isoleucine in 400 ml. of tetrahydrofuran at $40°-45°$ C is added gaseous phosgene until the solution becomes clear. The solution is then aspirated with nitrogen for 1 hour and then evaporated to dryness under reduced pressure.

The crude isoleucine-N-carboxyanhydride obtained in this fashion is dissolved in 300 ml. of acetonitrile, and to this solution is added 46.8 g. of dopamine hydrobromide dissolved in a mixture of 1000 ml. of acetonitrile and 800 ml. of water containing 8 g. of sodium hydroxide and 20.2 g. of sodium carbonate with a temperature of $-10°$ C.

The mixture becomes homogeneous and is allowed to react at $-10°$ for 2 hours, after which time 100 g. of ammonium sulfate is added. The solution separates into two phases. The aqueous phase is discarded. The acetonitrile phase is washed with 500 ml. of a 15% aqueous ammonium sulfate solution and again, the aqueous phase is discarded. The organic layer is dried over anhydrous sodium sulfate, filtered and stripped off solvent under reduced pressure to yield 50 g. of crude isoleucyldopamine. Thin-layer chromatography shows the desired compound to be present in over 90% yield with three major impurities amounting to less than 10% in total. The nmr spectrum is found to be consistent with the proposed structure.

Purification of the above crude material by standard chromatography and lyophilization yields the pure material melting, as a glass, at $85°-90°$ C, of which the chemical analysis closely corresponds with the calculated values for the above compound.

EXAMPLE II

Phosgene gas is bubbled into a mixture of 17.8 g. of L-alanine in 400 ml. of tetrahydrofuran at 40°–55° C until the solution becomes clear. This solution is worked up as in the previous example and the residue is redissolved in 300 ml. of acetonitrile and then added to a solution of 46.8 g. of dopamine hydrobromide dissolved in a mixture of 1000 ml. of acetonitrile and 800 ml. of water containing 8 g. of sodium hydroxide and 20.2 g. of sodium carbonate at a temperature of −10° C. Work-up of this material continues exactly as in Example I, producing a yield of 90% of L-alanyldopamine. The obtained crude material can easily be recrystallized from isopropanol to provide pure alanyldopamine, melting at 227°–32° C.

When in the above example the alanine is replaced by an equivalent amount of phenylalanine, the corresponding phenylalanyldopamine is obtained in a similar yield. Also, by using an equivalent amount of 3,4-di(-benzyloxycarbonyloxy)phenethylamine in place of dopamine and benzyloxycarbonyl-protected tyrosine in place of alanine, the correspondingly tri-protected tyrosyldopamine is obtained, although some of the protection in the tyrosyl moiety may have cleaved in the process of preparing the anhydride thereof. All protective groups can then be cleaved simultaneously in a standard reaction well known to those skilled in the art.

As will be seen from the above illustrations, the N-carboxyanhydride of the desired aminoacid can be prepared in situ, i.e., it can be obtained by simply gassing a solution of the free aminoacid with phosgene. There is no need to protect the N-terminus of the aminoacid and there is also no need to purify the anhydride so obtained. In most instances, isolation of the anhydride is not required, as long as any excess phosgene is removed or destroyed and the solvent qualifies as a reaction medium for the condensation to follow. Surprisingly, the dopamine does not require any protective groups on the hydroxy substitution although, benzyloxy derivatives thereof can be used where it is desired to obtain an aminoacyl derivative of the disubstituted dopamine. Such benzyloxy groups can easily be removed after the condensation has taken place, for instance by hydrogenation or other well known methods.

As demonstrated above, the aminoacyl dopamine derivatives can, by the process of this invention, be obtained in a single reaction vessel in a simple procedure that requires very little time. In fact, experience has proven that the new process enables the manufacture of the desired compounds at a fraction of the cost of other methods known from the prior art.

What is claimed is:

1. The process for making a compound of the formula

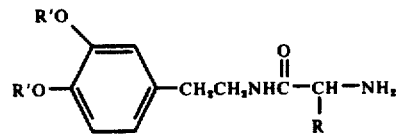

where R is hydrogen or an inert radical and R′ is hydrogen or benzyloxycarbonyl, consisting essentially in reacting the N-carboxyanhydride of a natural aminoacid of the formula $NH_2$-CHR-COOH wherein R has the above meaning with dopamine or its dibenzyloxycarbonyl analog in an inert, liquid reaction medium at a pH of 8–12.5 and a temperature of −10° C to 5° C and recovering the formed acyldopamine derivative of said formula I.

2. The process of claim 1 wherein said aminoacid and said dopamine or dibenzyloxydopamine are used in substantially equimolar amounts.

3. The process of claim 1 wherein said liquid reaction medium is water.

4. The process of claim 1 wherein said liquid reaction medium is acetonitrile.

5. The process of making a dopamine of the formula

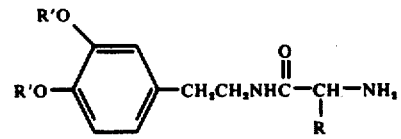

wherein R is H or an inert radical and R′ is H or benzyloxycarbonyl, consisting essentially in combining, at a temperature of between −10° C and 5° C, substantially equimolar amounts of dopamine or its dibenzyloxy analog with the N-carboxyanhydride of a natural aminoacid of the formula $NH_2CHR$—COOH wherein R is hydrogen, linear or branched loweralkyl, phenylalkyl, benzyloxycarboxyphenyl, benzyloxycarboxyalkyl, indolyl, methylmercaptoalkyl or pyrrolidyl in the presence of an inert, liquid reaction medium buffered to a pH of between 8 and 12.5.

6. The process of claim 5 wherein said R is an alkyl group of 1–4 carbons.

7. The process of claim 5 wherein said inert liquid is water.

8. The process of claim 5 wherein said inert liquid is acetonitrile.

9. The process of claim 5 wherein said R is benzyl.

10. The process of claim 5 wherein said reactants are combined at a temperature of −10° to +5° C and, after 30 min., the reaction mixture is allowed to adjust to room temperature.

* * * * *